United States Patent [19]

Cohnen

[11] 4,166,849
[45] Sep. 4, 1979

[54] PERUVOSIDE DERIVATIVES AND PROCESSES FOR THEIR PREPARATION

[75] Inventor: Erich Cohnen, Hamburg, Fed. Rep. of Germany

[73] Assignee: Beiersdorf Aktiengesellschaft, Hamburg, Fed. Rep. of Germany

[21] Appl. No.: 925,026

[22] Filed: Jul. 17, 1978

[30] Foreign Application Priority Data

Jul. 30, 1977 [DE] Fed. Rep. of Germany ....... 2734459

[51] Int. Cl.$^2$ .................. A61K 31/705; C07J 19/00
[52] U.S. Cl. .......................... 424/182; 536/7
[58] Field of Search ............... 424/182; 536/7

[56] References Cited
U.S. PATENT DOCUMENTS 4,088,757  5/1978  Petersen ..................... 536/7

FOREIGN PATENT DOCUMENTS 2548525  5/1977  Fed. Rep. of Germany ........... 536/7
2558208  7/1977  Fed. Rep. of Germany ........... 536/7

Primary Examiner—Johnnie R. Brown
Attorney, Agent, or Firm—Bierman & Bierman

[57] ABSTRACT

The present invention is directed to novel peruvoside derivatives having the formula

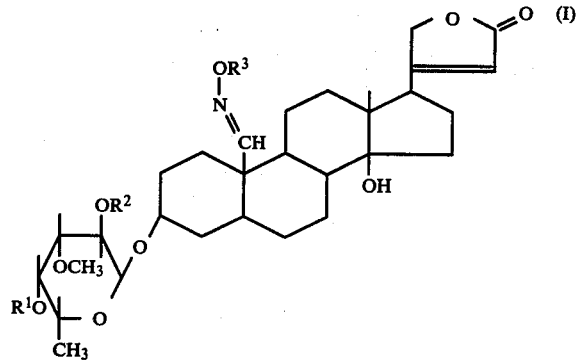

and the formula

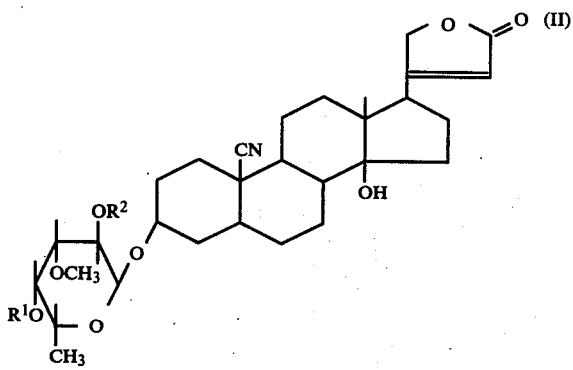

wherein $R^1$ and $R^2$ are the same or different and are selected from a hydrogen atom, an acyl group, an alkoxymethyl group and a carboalkoxy group wherein the alkyl portion of said groups has 1–4 carbon atoms and $R^3$ is an acyl group having 2–5 carbon atoms. Methods of preparation and suitable compositions are also disclosed. Said compounds and compositions are useful for the treatment of cardiac insufficiencies.

2 Claims, No Drawings

PERUVOSIDE DERIVATIVES AND PROCESSES FOR THEIR PREPARATION

BACKGROUND OF THE INVENTION

The novel compounds according to the present invention differ substantially from known, similarly constructed glycosides in that they contain, in the genin-portion of the molecule, a cyano group or an acylated oxime group. This group of compounds possesses valuable pharmacological properties. Used in appropriate doses, they provide improvement in the contractile power of the heart muscle and are, therefore, suitable in cardiac therapy, particularly for the treatment of cardiac insufficiencies.

Peruvoside is a naturally occurring glycoside which can be obtained, for example, from Apocynacea Thevetia neriifolia. It is well known that this glycoside has only limited usefulness in cardiac therapy because it provides for only moderate enteral resorption.

Another problem associated with peruvoside is the relative ease with which it is metabolized. Thus, when radio-marked peruvoside is injected in test animals, peruvosidic acid is one of the metabolites detected [Arzneim. Forsch. 18, 1605, (1968)]. It is also known that the aldehyde group of cardiac glycosides undergoes reduction in animals to form 19-hydroxy derivatives which are subject to further metabolic activity such as glucuronidation [Arch. Exp. Path. Pharmacol. 247, 71(1964) or Arch. Int. Pharmacodyn. 156, 489 (1965)].

On the other hand, the present peruvoside derivatives successfully overcome the deficiencies of the prior art compounds. More specifically, a significant improvement in enteral resorption is observed because the present compounds provide for etherification or esterification of the hydroxyl groups attached to the sugar portion of the molecule. This results in a reduction of the polarity of the molecule which is directly responsible for the desired increase in enteral resorption. Polarity reduction is also enhanced by the presence of the acylated oxime group.

By etherifying and esterifying the hydroxyl groups with the carboalkoxy, alkoxymethyl, and acyl groups of the present invention, the former groups are afforded protection until after resorption. The latter groups are easily metabolized subsequent to resorption.

Additionally, the acylated oxime compounds as shown in formula I and the tertiary cyano compounds of formula II provide for a reduced amount of cardioactive and cardioinactive metabolites as compared with the aldehyde group-containing peruvoside of the prior art.

SUMMARY OF THE INVENTION

The compounds of the present invention are peruvosides represented by the formula

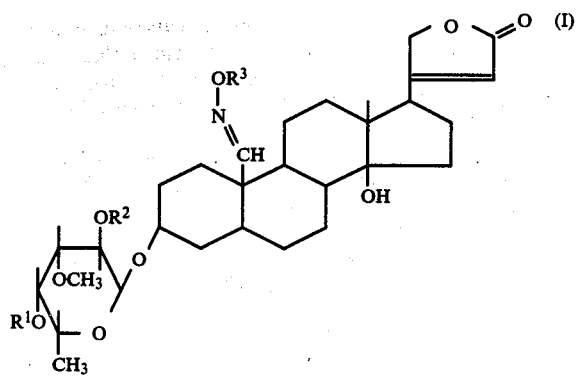

and 19 nor-10-cyano peruvosides represented by the formula

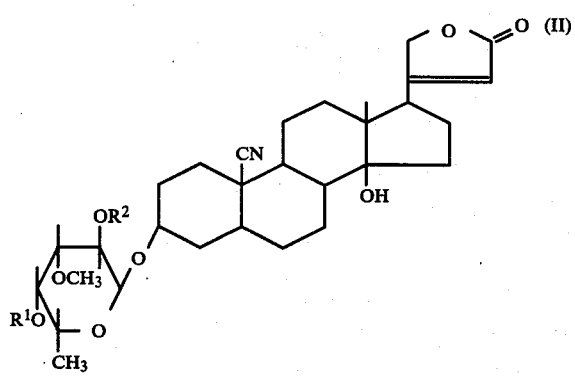

wherein $R^1$ and $R^2$ are the same or different and are selected from a hydrogen atom, an acyl group, an alkoxymethyl group, and a carboalkoxy group wherein the alkyl portion of said groups has 1–4 carbon atoms, and $R^3$ is an acyl group having 2–5 carbon atoms.

The acylated oximes represented by the compounds of formula I can be prepared in a known manner by utilizing the oximes represented by the formula III

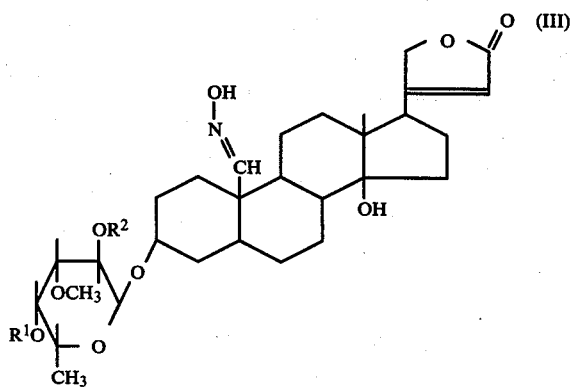

wherein $R^1$ and $R_2$ are the same as defined above.

These oximes are dissolved, for example, in a suitable solvent such as pyridine and then reacted with an excess of an appropriate acylating agent to maintain the desired member for $R^1$ and $R^2$ of formula I. Preferred acylating agents are acid anhydrides and acid halides which react with the oxime group at low to slightly elevated temperatures in a suitable solvent. Especially preferred are anhydrides of carboxylic acids having 2-5 carbon atoms.

Uniformly tri-acylated peruvoside oximes, wherein 2',4'-diacyl groups are the same as that attached to the oxime group, can be obtained from oximes with carboxylic anhydrides in pyridine at room temperature. Suitable anhydrides are those derived from carboxylic acids having 2-5 carbon atoms. If, for example, acetanhydride is used, then 2',4'-diacetyl oxime acetate is obtained.

The oximes of general formula III can be prepared in a known manner by treating 19-oxo-cardenolides of formula IV,

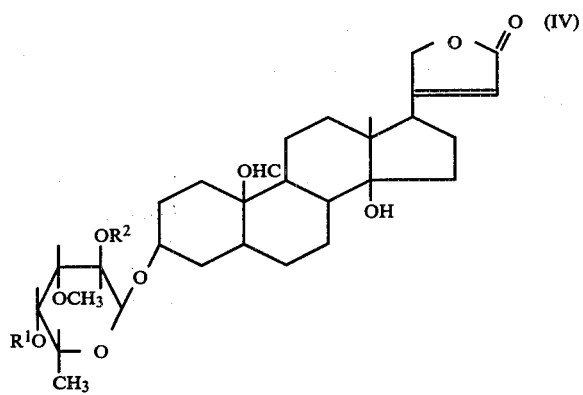

wherein $R^1$ and $R^2$ have the same meaning as defined above, with excess hydroxylamine-hydrochloride in a (1:1) pyridine/ethanol solution for 1-2 hours at 70° C. [M. F. Browne et al., J. Org. Chem. 22, 1320 (1957)]. The starting compounds used for the preparation of the oximes obtained in this manner are either the naturally occurring glycoside, peruvoside, or its derivatives wherein $R^1$ and $R^2$ are defined as above. These compounds can be obtained according to methods well known in the art.

The 19-nor-10-cyano compounds of formula II can be obtained in a known manner by dehydrating the oximes of general formula III. For example, dehydration can be accomplished with acetanhydride in pyridine as a solvent, according to the method described by [E. P. Oliveto et al. Journal Americ. Chem. Soc. 81 2833, (1959)]. The reaction is conducted for 1 to 2 hours at temperatures between about 80° C. and 120° C. The acylated oximes of formula I can be likewise reacted according to this method to produce the 19-nor-10-cyano compounds of formula II.

If the above-mentioned dehydration reaction is carried out with the oximes of formula III at room temperature, the uniformly tri-acylated compound 2',4'-diacetyl-peruvoside oxime acetate is obtained as an intermediate product.

Another dehydration reaction is accomplished with dicyclohexyl carbodiimide in the presence of copper (II) ions, pyridine and triethylamine according to the method of [E. Vowinkel and J. Bartel Chem. Berichte 107, 1221-1227 (1974)]. This reaction is carried out at room temperature, preferably by using methylene chloride as a solvent. The reaction time is about 15 hours.

There is an advantage in using the latter dehydration method. If the starting material of formula III has hydrogen atoms in the $R^1$ and/or $R^2$ position, acylation of the hydroxyl groups of the sugar portion of the molecule is not possible. Therefore, introduction of the substituents designated as $R^1$ and $R^2$ follows immediately without removal of the protective groups.

The acetyl groups attached to the sugar portion of the molecule in the former dehydration method can be partially or completely removed by saponification with $KHCO_3$ by selecting a suitable reaction time and temperature.

The new compounds of the present invention can be mixed with pharmacologically compatible substances such as carriers and/or diluents of the usual kind, e.g. milk sugar (lactose) gelatin, maize starch, stearic acid, ethanol, 1,2-propylene glycol, ethers of tetrahydrofurfurylalcohol and water. The selection of these substances is fully within the expertise of one having reasonable skill in the art. The dosage range of the compounds of the present invention varies from about 0.2 to 0.6 mg/day per person. Hence, solutions for injection purposes and pharmaceutical preparations to be given orally, such as dragees, pills or tablets, are within the scope of this invention.

The preparation of the present compounds is described below in more detail. These examples are for the purpose of illustration only and are not meant to limit the subject matter claimed in the generic claim of the present application.

EXAMPLE 1

19-oxime-peruvoside 3.0 g of peruvoside are heated for 3 hours at 70° C. with 0.55 g of hydroxylamine hydrochloride in 40 ml of pyridine and 40 ml of ethanol. The peruvoside oxime is obtained in a quantitative yield as a foam.

EXAMPLE 2

2',4'diacetyl-peruvoside-19-oxime acetate.

3.0 g of peruvoside oxime are dissolved in 30 ml of pyridine and, after addition of 7.5 ml of acetanhydride, the resulting solution was left to stand for 24 hours at room temperature. Subsequently, water is added and the product is evaporated in a vacuum. The residue obtained is dissolved in chloroform and the organic phase is repeatedly extracted with water and dried. After recrystallization from acetic ethyl ester/diisopropylether, 1.5 g of oxime acetate was obtained having a m.p. of 145°-146° C.

EXAMPLE 3

19-nor-10-cyano peruvoside

The oxime obtained according to Example 1 is dissolved in 100 ml of methylene chloride and 5 ml of pyridine. Then, 300 mg of $CuSO_4.5H_2O$ and 2 ml of triethylamine are added followed by 1.36 g of dicyclohexyl carbodiimide. After stirring for 20 hours, the products are filtered off, evaporated in a vacuum and the residue fractioned with a (9:1) chloroform/methanol solution in a silica gel column. The yield was 2.1 g and the product had a m.p. of 214°-217° C.

The same 19-nor-10-cyano peruvoside is also obtained by saponification of the 2',4'-diacetyl compound of Example 4 by heating the latter in an aqueous methanol solution with $KHCO_3$ for 48 hours at 50° C.

EXAMPLE 4

2',4'-diacetyl-19-nor-10-cyano peruvoside 1.7 g of peruvoside oxime are dissolved in 20 ml of pyridine and 3 ml of acetanhydride are added thereto.

The mixture is then heated to a boil for 1 hour. Water is added to the reaction mixture and the solvent is removed in a vacuum. The residue is taken up in methylene chloride, extracted with water, dried, and evaporated in a vacuum. After recrystallization from acetic ethyl ester/diisopropyl ether, 1.3 g of 2',4'-diacetyl-19-nor-10-cyano peruvoside is obtained having a m.p. of 251° C.

EXAMPLE 5

2',4'-diacetyl-19-nor-10-cyano peruvoside 900 mg of 19-nor-10-cyano peruvoside are acylated with 2 ml of acetanhydride at room temperature in 5 ml of pyridine. After processing as described in Example 4, 800 mg of the acylated compound is obtained which is recrystallized from acetic ethyl ester/diisopropyl ether having a m.p. of 245°-248° C.

EXAMPLE 6

2'-acetyl-19-nor-10-cyano peruvoside 200 mg of 19-nor-10-cyano peruvoside are dissolved in 3 ml of pyridine and then treated at 0° C. with 0.05 ml of acetanhydride. After 3 hours the resulting product is processed as described in Example 4, and the residue is chromatographed in a silica gel column with a (9:1) chloroform/methanol solution. The yield of the product is 70 mg having a m.p. of 200°-201° C.

EXAMPLE 7

4'-acetyl-19-nor-10-cyano peruvoside 400 mg of 2',4'-diacetyl-19-nor-10-cyano peruvoside are dissolved in 20 ml of methanol. The mixture is then mixed with 300 mg of $KHCO_3$ in 10 ml of $H_2O$ and left standing for 2 days at room temperature. After neutralization with dilute acetic acid, the product is extracted with chloroform. The residue of the organic phase is then mixed with some methanol. 300 mg of crystalline monoacetate of the 19-nor-10-cyano peruvoside is obtained having a m.p. of 207°-208° C. A NMR spectroscopic investigation shows that the resulting product is the 4'-acetyl compound.

EXAMPLE 8

2',4'-dibutyroyl-19-nor-10-cyano peruvoside 200 mg of 19-nor-10-cyano peruvoside are acylated with 1 ml of butyric acid anhydride in 2 ml of pyridine and processed according to the procedure set forth in Example 4. The product obtained had a m.p. of 195°-200° C.

EXAMPLE 9

(a) 2'-ethoxycarbonyl and (b) 2',4'-diethoxy-carbonyl-19-nor-10-cyano peruvoside A solution of 200 mg of 19-nor-10-cyano peruvoside in 10 ml of pyridine is mixed at 5°-10° C. with 2 ml of ethylchloroformate and stirred for 5 hours at room temperature. After processing as described in Example 4, the two compounds (a) and (b) are separated by thick layer chromatography ($CHCl_3$/MeOH 95:5).

(a) 2'-ethoxycarbonyl-19-nor-10-cyano peruvoside was recrystallized in ethylacetate/ether and the final product had a m.p. of 251°-253° C.

(b) 2',4'-diethoxycarbonyl-19-nor-10-cyano peruvoside resulted in a final product having a m.p. of 220°-225° C.

EXAMPLE 10

2',4'-dimethoxymethyl-19-nor-10-cyano peruvoside 500 mg of 19-nor-10-cyano peruvoside is dissolved in 10 ml of dioxane. Then, 2.5 ml of dimethylaniline are added thereto followed by the dropwise addition of 1.2 ml of chlorodimethyl ether. The resulting mixture is stirred for 6 hours at room temperature. Then, the product is diluted with chloroform, extracted with 5% HCl, shaken successively with NaOH and water, and evaporated until dried. After thick layer chromatography of the residue is completed, 260 mg of 2',4'-dimethoxymethyl-19-nor-10-cyano peruvoside as foam is obtained. IR spectrum (KBr): 1755, 1780 (C=O), 2230 (C≡N) 1030, 1105 (C—O—C) $cm^{-1}$.

What we claim is:

1. A compound of the formula

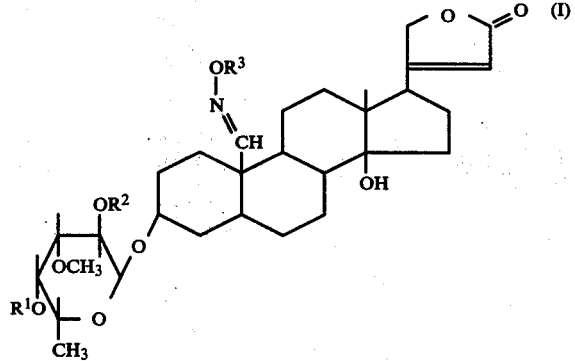

or of the formula

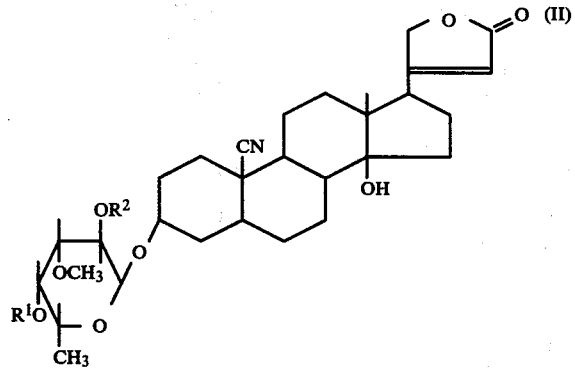

wherein $R^1$ and $R^2$ are the same or different and are selected from a hydrogen atom, an acyl group, an alkoxymethyl group, and a carboalkoxy group wherein the alkyl portion of said groups has 1–4 carbon atoms, and $R^3$ is an acyl group having 2–5 carbon atoms.

2. A pharmaceutical composition comprising an effective amount of the compound of claim 1 and a pharmaceutically acceptable carrier.

* * * * *